(12) United States Patent
Faber et al.

(10) Patent No.: US 8,399,831 B2
(45) Date of Patent: Mar. 19, 2013

(54) FORMING AN IMAGE WHILE MILLING A WORK PIECE

(75) Inventors: Jacob Simon Faber, Eindhoven (NL); Remco Theodorus Johannes Petrus Geurts, Oss (NL)

(73) Assignee: FEI Company, Hillsboro, OR (US)

( * ) Notice: Subject to any disclaimer, the term of this patent is extended or adjusted under 35 U.S.C. 154(b) by 343 days.

(21) Appl. No.: 12/732,924

(22) Filed: Mar. 26, 2010

(65) Prior Publication Data

US 2010/0243889 A1 Sep. 30, 2010

(30) Foreign Application Priority Data

Mar. 27, 2009 (EP) .................................... 09156391

(51) Int. Cl.
*H01J 37/305* (2006.01)
*H01J 37/30* (2006.01)

(52) U.S. Cl. ..... 250/306; 250/307; 250/310; 250/396 R; 250/397; 250/492.2

(58) Field of Classification Search ............... 250/493.2, 250/440.11, 442.11, 492.1, 492.21
See application file for complete search history.

(56) References Cited

U.S. PATENT DOCUMENTS

| | | | |
|---|---|---|---|
| 4,629,898 A | | 12/1986 | Orloff et al. |
| 5,093,572 A | * | 3/1992 | Hosono ........................ 250/310 |
| 5,273,935 A | | 12/1993 | Morimoto et al. |
| 5,525,806 A | * | 6/1996 | Iwasaki et al. ........... 250/492.21 |
| 5,948,217 A | | 9/1999 | Winer et al. |
| 5,952,658 A | * | 9/1999 | Shimase et al. ................. 850/63 |
| 7,391,039 B2 | | 6/2008 | Kitamura et al. |
| 7,531,796 B2 | * | 5/2009 | Tashiro et al. ................. 250/306 |
| 7,829,870 B2 | * | 11/2010 | Frosien ....................... 250/492.1 |
| 7,897,936 B2 | * | 3/2011 | Shichi et al. ............. 250/442.11 |
| 8,143,594 B2 | * | 3/2012 | Wanzenboeck et al. . 250/440.11 |
| 2006/0037182 A1 | * | 2/2006 | Roy et al. ..................... 29/25.01 |
| 2006/0286772 A1 | * | 12/2006 | Pearl ............................ 438/460 |

(Continued)

FOREIGN PATENT DOCUMENTS

| | | |
|---|---|---|
| EP | 2149897 | 2/2010 |
| WO | 2008049133 | 4/2008 |

(Continued)

OTHER PUBLICATIONS

Lucille A Giannuzzi, Fred A Stevie: Introduction to Focused Ion Beams. p. 276-293. 2005. Springer. XP00250689.*

(Continued)

*Primary Examiner* — Nikita Wells
*Assistant Examiner* — Johnnie L Smith
(74) *Attorney, Agent, or Firm* — Scheinberg & Associates, PC; Michael O. Scheinberg

(57) ABSTRACT

Dual beam instruments, comprising a Scanning Electron Microscope (SEM) column for imaging and a Focused Ion Beam (FIB) column for milling, are routinely used to extract samples (lamellae) from semiconductor wafers. By observing the progress of the milling with the SEM column, end pointing of the milling process can be performed.
The invention offers an alternative solution to this problem, in which an instrument with only a FIB column is used.
For milling a lamella to its final thickness of, for example, 30 nm, the focused ion beam 100, is scanned repeatedly along the lamella. It is found that while milling the lamella a signal can be derived from the lamella that is sufficient for end pointing. No additional electron beam for inspection is needed.

23 Claims, 5 Drawing Sheets

U.S. PATENT DOCUMENTS

| | | | |
|---|---|---|---|
| 2007/0087572 A1* | 4/2007 | Le Roy et al. | 438/712 |
| 2008/0314871 A1 | 12/2008 | Toth et al. | |
| 2009/0309018 A1 | 12/2009 | Smith et al. | |
| 2011/0163068 A1* | 7/2011 | Utlaut et al. | 216/66 |

FOREIGN PATENT DOCUMENTS

| | | |
|---|---|---|
| WO | 2008049134 | 4/2008 |
| WO | 2008051937 | 5/2008 |

OTHER PUBLICATIONS

Giannuzzi, Lucille A. et al., 'Introduction to Focused Ion Beams,' Springer, 2005, pp. 2765-2293.

Orloff, J. et al., 'High Resolution Focused Ion Beam,' Applications of Focused Ion Beams, 2003, pp. 245-266.

* cited by examiner ent environment,
FORMING AN IMAGE WHILE MILLING A WORK PIECE The invention relates to a method of milling and imaging a work piece, the work piece showing a face, the method comprising:
  placing the work piece in an evacuated environment,
  directing a focused particle beam to the surface,
  scanning said beam over the surface in a predetermined pattern to irradiate points of the work piece, thereby milling the work piece,
  acquiring a signal from a detector detecting radiation emerging from the work piece in response to the particle beam impinging on the work piece, and
  storing data derived from the signal in a computer memory, the data thus forming a representation of a face of the work piece.

The invention further relates to software for performing the method according to the invention.

Such a method is known from International Application PCT/US2007/082159.

In e.g. the semiconductor industry samples are taken from semiconductor wafers, for inspection in e.g. a Transmission Electron Microscope (TEM). Such samples inspected in the TEM are typically rectangular samples with sides in the order of 10 μm and a thickness of less than 50 nm, preferably 30 nm, although other sizes and thicknesses may be used. Such a sample can be taken from the wafer by milling the wafer, leaving a thin membrane that is taken from the wafer for further processing and/or inspection.

It is noted that milling in this context includes sputtering and etching. Milling is typically done in a Focused Ion Beam apparatus (FIB), in which a focused ion beam is directed to the wafer for milling.

The milling speed is often enhanced by directing a jet of an appropriate fluid to the wafer with a Gas Injection System (GIS) while milling the work piece, so that a layer of this fluid adsorbs to the surface of the wafer. The fluid causes enhanced milling or etching when the wafer and the adsorbed fluid is irradiated by the ion beam.

The thin membrane, also known as lamella, as freed from the wafer is often too thick to be inspected in the TEM, and the further processing therefore typically comprises thinning the sample to a final thickness of typically less than 50 nm, often in the range of 20-40 nm thick.

The known International Application describes how a lamella is freed from a work piece in the form of a semiconductor wafer. The wafer is introduced in a FIB and fiducials are formed in the surface of the wafer, one set of fiducials for coarse positioning and one set of fiducials for fine positioning. Further a protective layer is locally added at the position where the lamella is to be formed so as to protect the lamella from unwanted exposure to the ion beam. Two trenches are formed in the wafer by directing an ion beam with a relatively high beam current to the surface of the wafer in such a manner that a thin membrane separates the two trenches. The position of the trenches with respect to the ion beam is, during the milling, repeatedly checked by measuring the position of the coarse fiducials. In this way drift of the work piece with respect to the ion beam is eliminated. When the trenches are deep enough, the membrane can be thinned. The thinning is done by adjusting the ion beam to a lower beam current, and measuring the position of the ion beam with respect to the fine fiducials. The membrane is then locally thinned by scanning the beam almost parallel over the surface of the membrane, resulting in so-named 'polishing' of the membrane.

As known to the person skilled in the art, imaging of a wafer with a FIB comprises directing a focused ion beam to the wafer and scanning the beam over the surface of the wafer in a predetermined pattern, e.g. in a raster. In response to the impinging ion beam radiation, such as electrons and secondary ions, emerges from the wafer. That the beam mills the surface during the imaging is an unwanted side effect, as imaging is preferably done without damaging the fiducials.

It is noted that for forming an image a single scan suffices, although repeated scanning may be used to improve the signal-to-noise ratio.

The known International Application describes imaging the surface of the wafer to determine the position of the fiducials so as to position the beam correctly to the portions of the wafer to be milled.

The known International Application further describes the final thinning of a membrane or lamella, the final thinning often referred to as a clean up cut or a cleaning cross section. In this final thinning the ion beam is scanned one line at a time toward a feature of interest. With this cutting pattern the beam executes a set of line cuts in serial mode so as to gradually step the line cut into the exposed surface to clean it. When the number of line cuts milling away material arrive at the bottom of the trench, the line is stepped in the direction of the other trench, and a fresh layer is milled from the lamella.

A disadvantage of the known method it that no image is made of the face exposed by the milling, and that any end pointing must be based on the image as formed from the surface of the wafer.

The invention intends to provide a solution for this.

To this end the invention is characterized in that the beam impinges on the work piece substantially parallel to the face of the work piece, the irradiated points form a single curve that is repeatedly scanned, during each scan material is milled from a different distance from the surface, and the computer memory stores the data for multiple scans of the curve over the work piece, as a result of which the face is in one direction defined by the direction of the beam of particles and in the other direction defined along the curve.

The invention is based on the insight that, by detecting radiation generated while repeatedly milling a single line or curve, each line corresponds with a line or curve more removed from the surface. Therefore for a beam impinging perpendicular to a horizontal surface, a vertical face (parallel to the direction of the impinging beam) is imaged. This is in contrast to the prior art fashion of imaging, where a beam impinging vertically on a horizontal surface results in a horizontal face (parallel to the surface) being imaged.

It is noted that the scanning of the work piece with a curve is known, as described before, resulting in a series of line cuts. However, this was never combined with FIB imaging while milling the milled face. Instead FIB imaging is used for imaging the surface, where the fiducials are located.

It is further noted that imaging the milled face is known from instruments that mill using an ion beam and image with an electron beam, the electron beam angled with respect to the ion beam and intersecting the ion beam at the position of the work piece. These instruments are well accepted in the industry, but clearly are more expensive than an apparatus having only a FIB column.

It is worth mentioning that the quality of the images are less than the quality of surface images according to the prior art. This is due to the fact that radiation from the deeper portions of the trench is not detected with the same efficiency as radiation generated at or near the surface.

A further deterioration of the image is caused by the glancing way in which the beam scans over the lamella. As a result also parts of the lamella that are already cleaned (polished, milled) are marginally irradiated by the beam and thus generate secondary radiation that is detected. In other words: when milling and imaging parts of the lamella removed from the surface, also the part of the face between the surface and the line being milled contributes to the imaged points and a sort of cross-talk between the milled line and the part of the face between the milled line and the surface occurs.

In an embodiment of the method of the invention the beam of particles impinges substantially perpendicular to the surface.

Normally a lamella perpendicular to the surface of the work piece is excavated. This demands an ion beam perpendicular to the surface.

In another embodiment of the method of the invention the data is used to form an image.

The data representing a view of the milled face may be used to form an image on a display or any other imaging device, such as a printer.

In still another embodiment of the method of the invention the curve is a line segment, as a result of which the face is a rectangular face.

Here a rectangular face is imaged by repeatedly scanning a line.

It is noted that a rectangular face may also be formed by scanning a line segment in alternate directions, that is: in a serpentine fashion.

In yet another embodiment of the method of the invention the curve is a loop, as a result of which the face is a curved face.

In a further embodiment of the method of the invention the loop is a circle, as a result of which the face is a cylindrical face.

In another embodiment of the method of the invention the detected radiation comprises charged particles emerging from the work piece.

Normally secondary electrons are detected with, for example, an Everhart-Thornley detector or a photodiode equipped to detect charged particles. However, other types of detectors for detecting secondary electrons and/or, for example secondary ions, are known to the person skilled in the art.

In yet another embodiment of the method of the invention the focused particle beam is a focused charged particle beam.

Focused beams of charged particles, such as electrons or ions, can be focused by electrostatic filed or magnetic field and scanned by electric or magnetic deflectors. Sources for such beams are well known, and columns for delivering such focused and scanned beams are readily available.

In still another embodiment of the method of the invention the milling comprises gas assisted milling or gas assisted etching.

As known to the person skilled in the art, in a FIB the work piece is normally placed in a specimen chamber with a pressure of less than 1 mbar, typically $10^{-3}$ mbar or less. By directing a jet of etchant fluid, such as $XeF_2$ (xenon difluoride) to the work piece, a layer of the fluid adsorbs to the work piece and enhances the milling of the beam. In this way even an electron beam, that does not mill by itself, can be used for etching a work piece.

In still another embodiment of the method of the invention the data stored in the computer memory is compared to other data to determine an endpoint action.

The other data to which the stored data is compared can be data collected while observing another lamella. The comparison can be done automatically, that is: by a computer, using for example image recognition techniques, or the comparison can be performed by an operator, comparing an image formed from the data with another image or CAD model.

In a further embodiment of the method of the invention the other data is data generated using a CAD model.

In another embodiment of the method of the invention the curve is build up of a number of dwell points, the beam of particles directed to each of the dwell points for a predetermined dwell period, after which the beam of particles is directed to the next dwell point.

It is not necessary for the beam to travel along the curve at a constant speed. Jumping from point to point is an alternative that is often used with the scan generators and image memory available today.

In a further embodiment of the method of the invention for each dwell period one data-point is stored in the computer memory.

In another embodiment of the method of the invention each dwell period is divided into a number of sub-dwell periods, each sub-dwell period resulting in a data-point in the computer memory, each data-point corresponding to a different distance from the surface.

When the beam is directed to one point of the curve, it drills into the material, progressively milling away material that is further and further removed from the surface. The information acquired during one such dwell period can be divided in sub-dwell periods, the signal of each period stored in a different memory location, each subsequent location representing a position further removed from the surface.

In still another embodiment of the method of the invention, prior to directing the beam to a point on the curve, an adjacent point is milled, the adjacent point located at a position that, when directing the beam to the point on the curve, the beam does not hit the part of the face between the surface of the work piece and the part of the work piece that is milled.

By first milling a point close to the already milled face and then removing the beam slightly from the already milled face, the beam, that is glancing over the milled face, does not, or at least to a lesser degree, generate secondary radiation of the part of the face already milled, that is: the part of the face between the position where the beam mills the work piece and the surface of the work piece.

it is noted that, as the beam is parallel to the face while milling the face, the signal while milling a point always includes some signal of the milled face between the position where the actual milling is taking place and the surface.

BRIEF DESCRIPTION OF THE DRAWINGS

The invention is now described with reference to figures in which the identical reference numerals denote corresponding elements. Here:

FIG. 1 shows a particle beam in the form of an ion beam 100 impinging substantially perpendicular to the surface of a work piece in the form of a wafer surface 101. In the surface two sets of fiducials, a set of high precision fiducials 102a and a set of coarse fiducials 102b are milled. A protective layer 103 of e.g. tungsten or platinum is deposited on the surface. Two trenches 104 are milled, leaving a thin membrane or lamella 105 between them.

Figure 1:
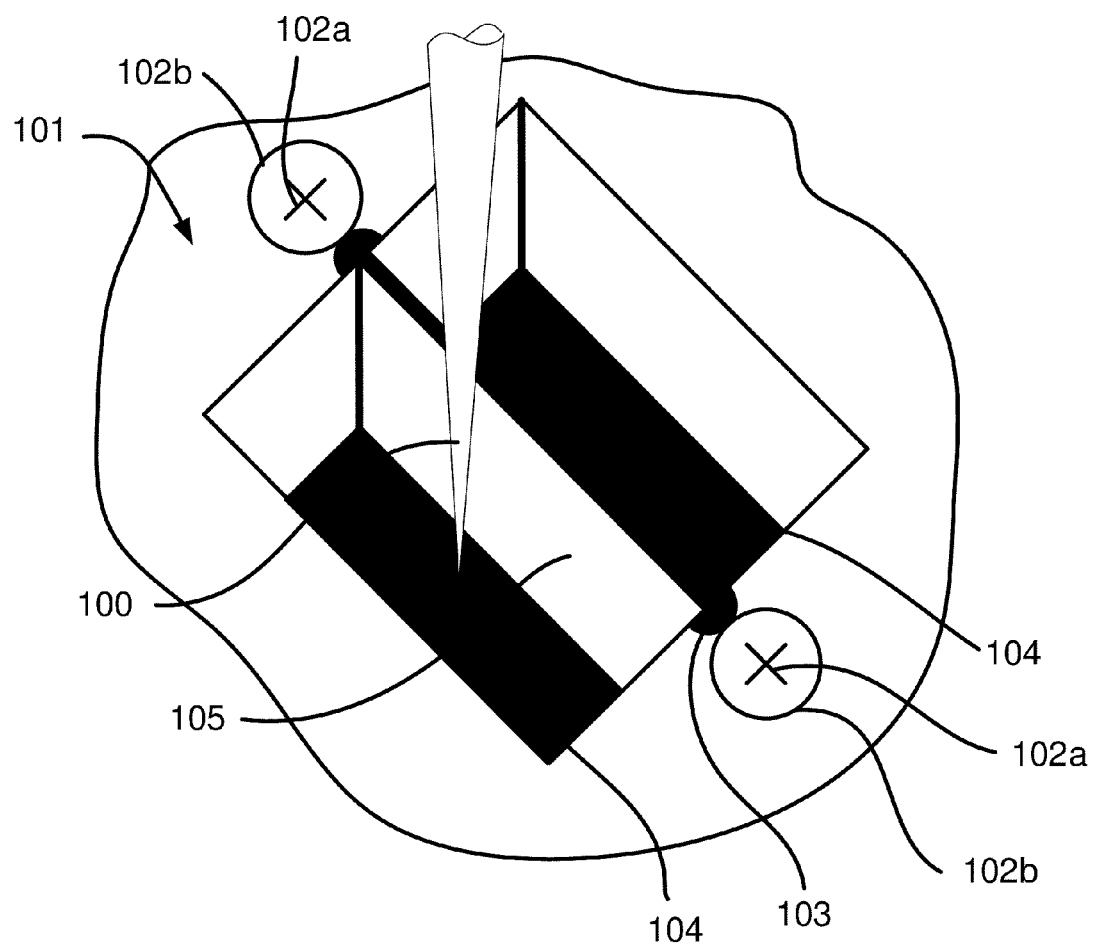
FIG. 1 schematically shows a wafer surface in which two trenches are milled.

The ion beam, such as a gallium ion beam produced by an ion column, comprises ions with an energy of e.g. 50 keV. Other types of ions, and other energy of the ions may be used. The ion beam is focused in a focus with a diameter of, for example, between 1 and 10 nm. Where the beam hits the surface material is sputtered away. In this way trenches may be milled in the surface by scanning the beam over the surface in, for example, a rectangular pattern. Often the process of scanning the beam over the surface is repeated several times, the trenches exposing deeper layers after each pass.

Before digging the trenches two sets of fiducials are milled in the surface, a set of coarse fiducials 102b and a set of fine fiducials 102a. These fiducials are used to position the beam with respect to the work piece when milling, and to eliminate the effects of, for example, drift. To define the relative position of work piece and particle beam an image is made of the surface, including the fiducials. By now determining the position of the fiducials in the image, the position of the image (the field of view) with respect to the fiducials is determined. When the work piece drifts with respect to the beam, the fiducials will drift in the image as well. By now changing, for example, the centre of the field of view, the effect of drift is eliminated. Re-positioning the field of view can be done on a regular basis, based on, for example, the amount of drift expected.

A protective layer is deposited on the wafer surface at that part of the surface that will be part of the thin membrane or lamella. Depositing a layer using an ion beam is known per se and is known as Ion Beam Induced Deposition (IBID). For depositing a metallic layer on a work piece, a jet of a precursor fluid, such as a metallo-organic gas, is directed to the work piece with a Gas Injection System (GIS) while the work piece is placed in a vacuum. A layer of the precursor gas adsorbs to the surface of the work piece. Exposing the work piece with the adsorbed layer to the ion beam results in a decomposition of the precursor molecules, as a result of which the metallic component is bonded to the surface. The rest of the organo-metallic molecule, forming more volatile product, desorbs from the surface and is pumped by the vacuum system of the apparatus.

It is noted that the ion beam used for deposition also causes some milling, but that the parameters such as ion beam current density, ion energy, the amount of fluid direct to the work piece, etc, the deposition can be made much higher than the milling.

This protective layer protects the top of the lamella against unwanted effects of the beam. It should be noted that, due to for example beam aberrations, the current density profile of the ion beam approaches a Gaussian curve, the diameter of the beam corresponding to, for example, the Full Width at Half Maximum (FWHM) value. Therefore some sputtering and/or implantation of ions at a distance removed from the centre of the beam may otherwise occur.

After depositing the protective layer on the surface of the wafer, the beam is scanned over the surface, irradiating two rectangles. Material is sputtered away at these irradiated positions, and two trenches 104 are formed, leaving the lamella between the two trenches.

It is noted that, although the process is here depicted to result in two trenches with a flat bottom, often the trench has a form in which the deepest part is near the lamella, while the trench at a position further removed from the lamella is shallower.

Figure 2:
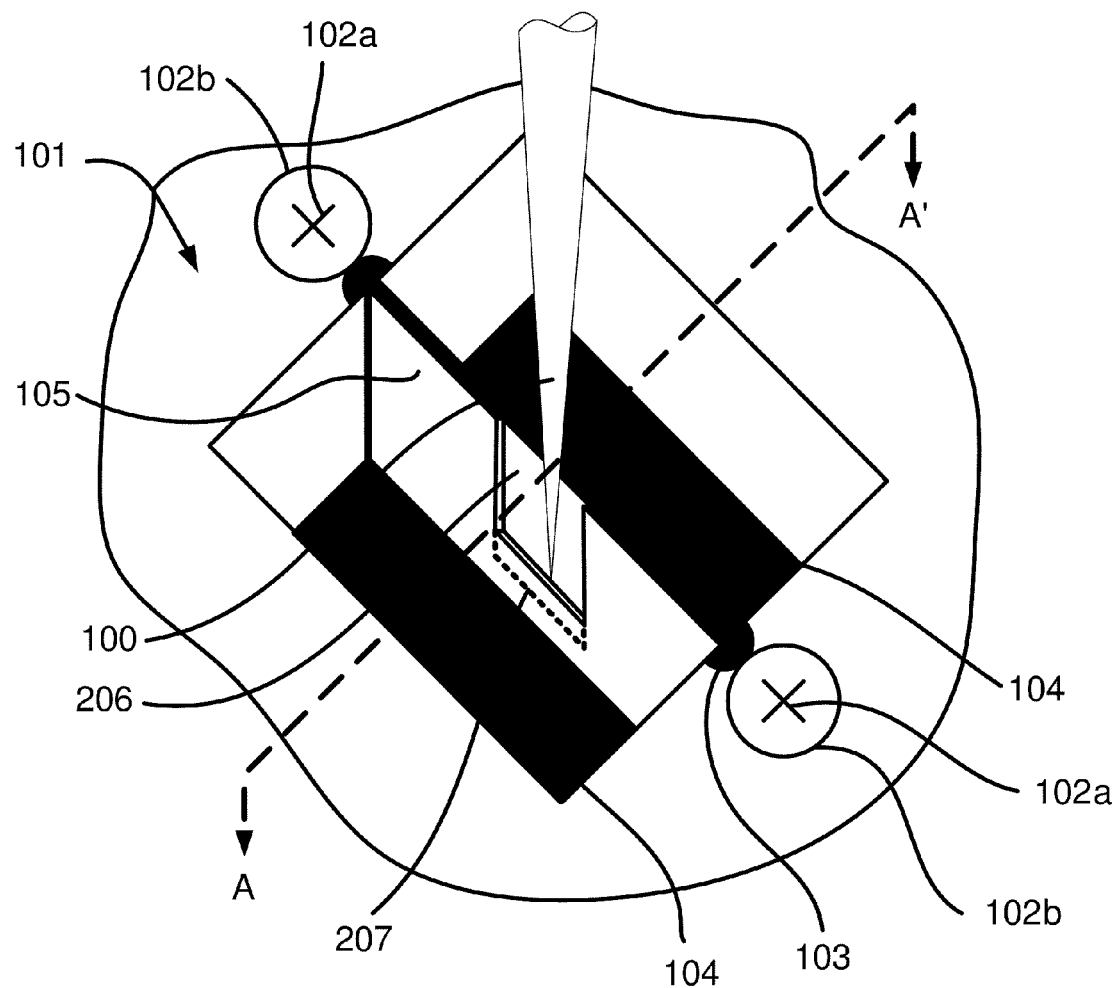
FIG. 2 schematically shows a lamella that is locally thinned.

FIG. 2 schematically shows a lamella that is locally thinned.

FIG. 2 can be thought to depict the wafer in a process step following the process step shown in FIG. 1. The lamella 105 is locally thinned, leaving a thinned part 206. For this local thinning, also referred to as polishing, the beam is directed to an edge of the lamella and a line segment is scanned repeatedly, as a result of which a thin strip of material is removed per scan. By repeatedly scanning the line segment a thin layer is removed, until the last strip 207 is removed.

It is noted that a lamella can be extracted from the wafer by cutting away the material near the fiducials and undercutting the bottom of the lamella. The lamella may be for example be glued or soldered to a manipulator before separating it from the wafer, or it may for example be soldered, glued, electrostatically or otherwise connected to a manipulator after separation. A lamella that is still connected at the bottom to the wafer may also be broken free from the wafer.

Figure 3:
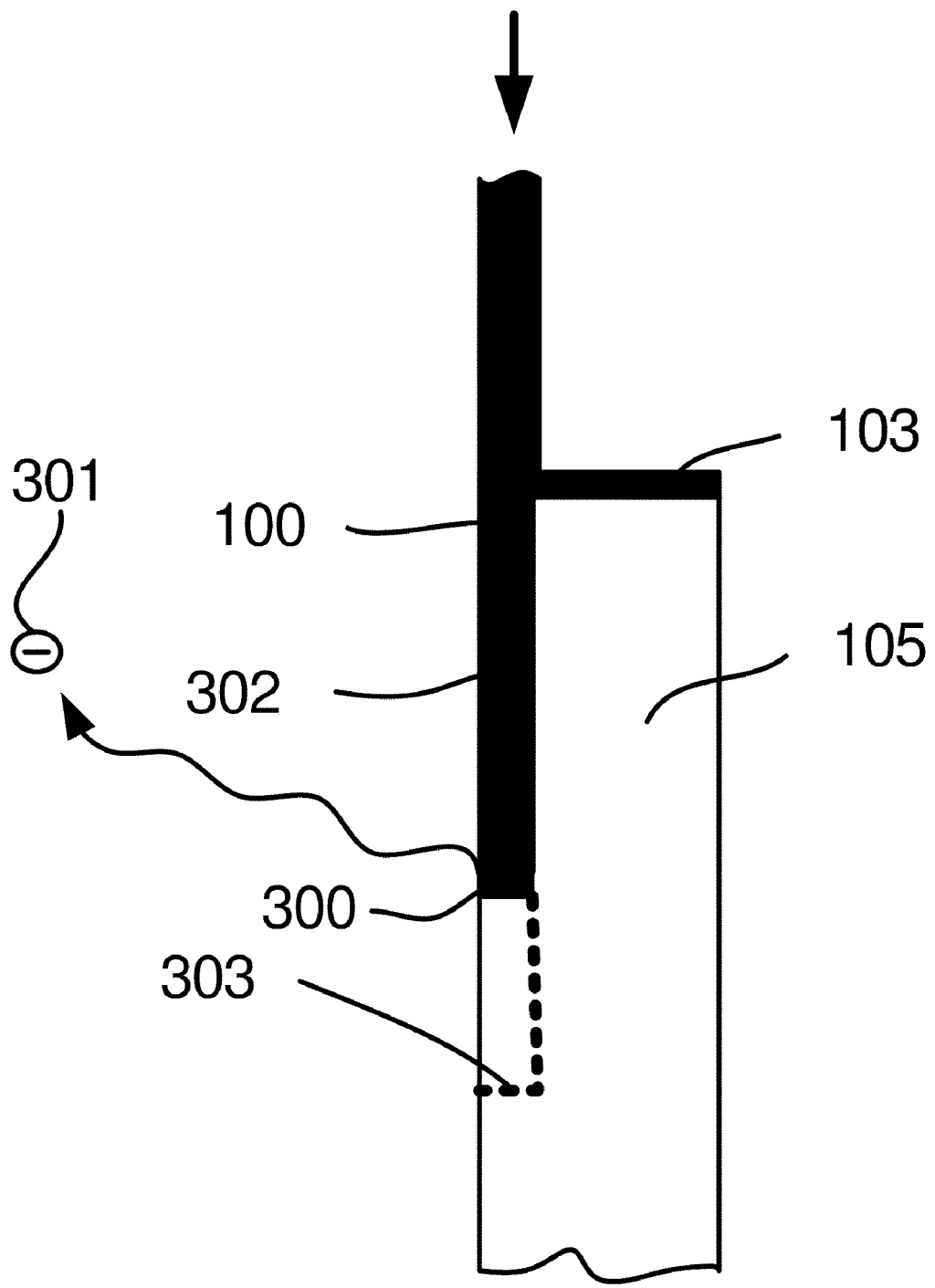
FIG. 3 schematically depicts a view along line AA' as shown in FIG. 2.

A view along line AA' is shown in FIG. 3.

FIG. 3 schematically depicts a view along line AA' as shown in FIG. 2.

FIG. 3 shows the lamella 105 with a protective layer 103, the lamella irradiated by ion beam 100. The ion beam is scanned over the wafer along a line perpendicular to the plane of this drawing. The beam is shown at the moment that it impinges on the lamella at position 300, where it mills material. The milling causes the ejection of secondary particles, such as a secondary electron 301 that can be detected by the detection means of the apparatus. Because the beam glances over the lamella, also some ions will impinge on the already polished part of the face 302, and parts of the wafer material located on this exposed face will contribute to the signal detected by the detection means.

The polishing of this face can be stopped when sufficient strips of material are removed and the bottom of the polishing face 303 is reached.

It is noted that, although the beam is a focused beam, the opening angle used in milling is normally so small (typically several mrad), that no change in beam diameter can be observed over the length to be milled (typically 5-15 µm).

FIG. 4 schematically shows a comparison of the image as obtained with a prior art electron beam and an image made according to the invention.

Figures 4A, 4B:
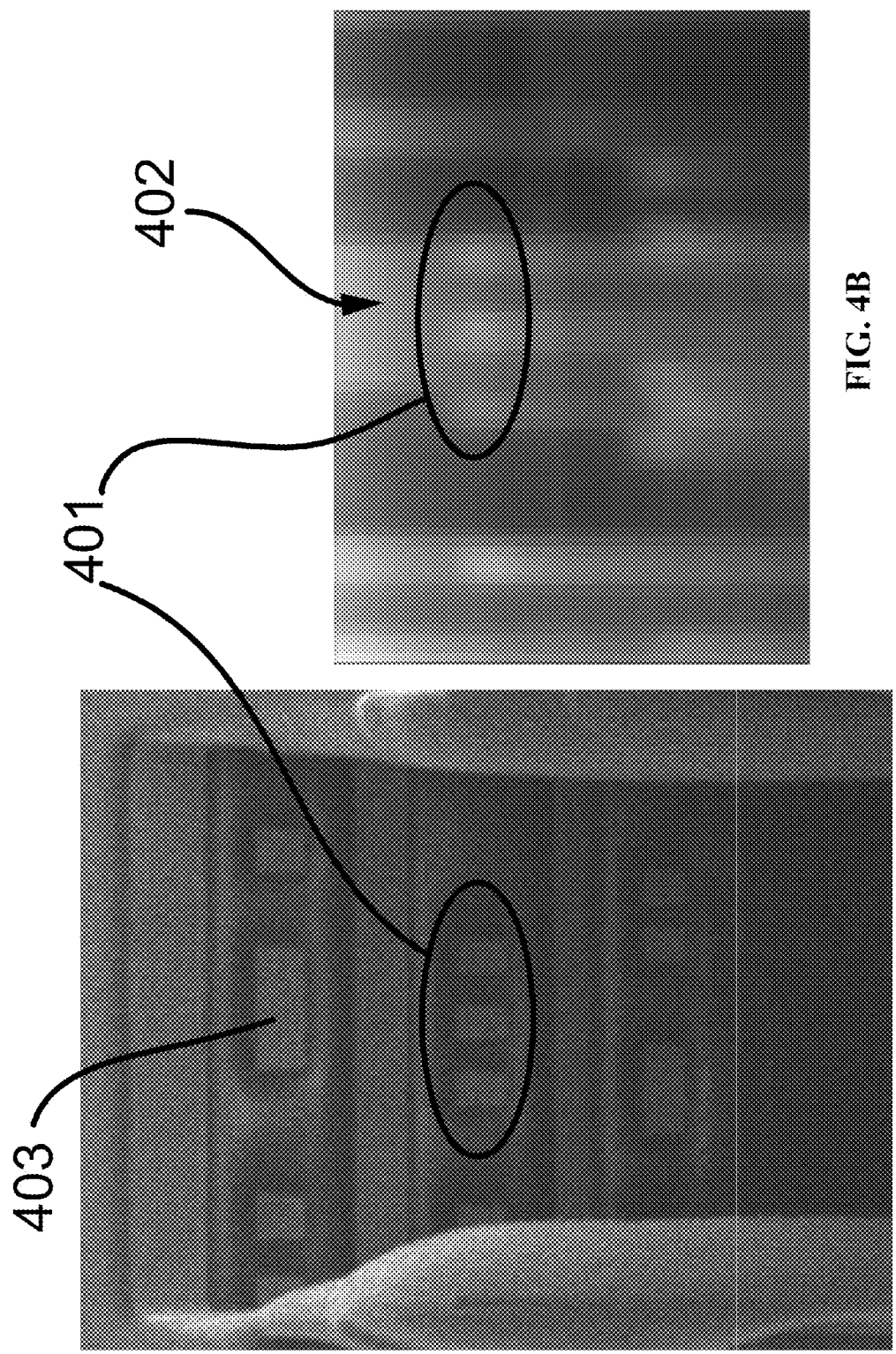
FIG. 4A and FIG. 4B schematically show a comparison of the image as obtained with a prior art electron beam and an image made according to the invention, and FIG. 5 schematically shows an apparatus equipped to perform the method according to the invention.

FIG. 4A shows an image as is made in a so-named dual beam instrument, in which the milling and polishing is done with an ion beam and the progress of the polishing is observed with an electron beam directed to the face 105 under an angle. The image shows the typical image quality and image resolution obtained by a SEM.

FIG. 4B shows an image made in a FIB, using the method according to the invention. The image quality is much worse than that obtained with the electron beam shown in FIG. 4A, but is found to be sufficient for end pointing.

It is noted that the smearing in the vertical direction that can be seen in image 4B is a result of the contribution of the already exposed face 302, as explained before.

Figure 5:
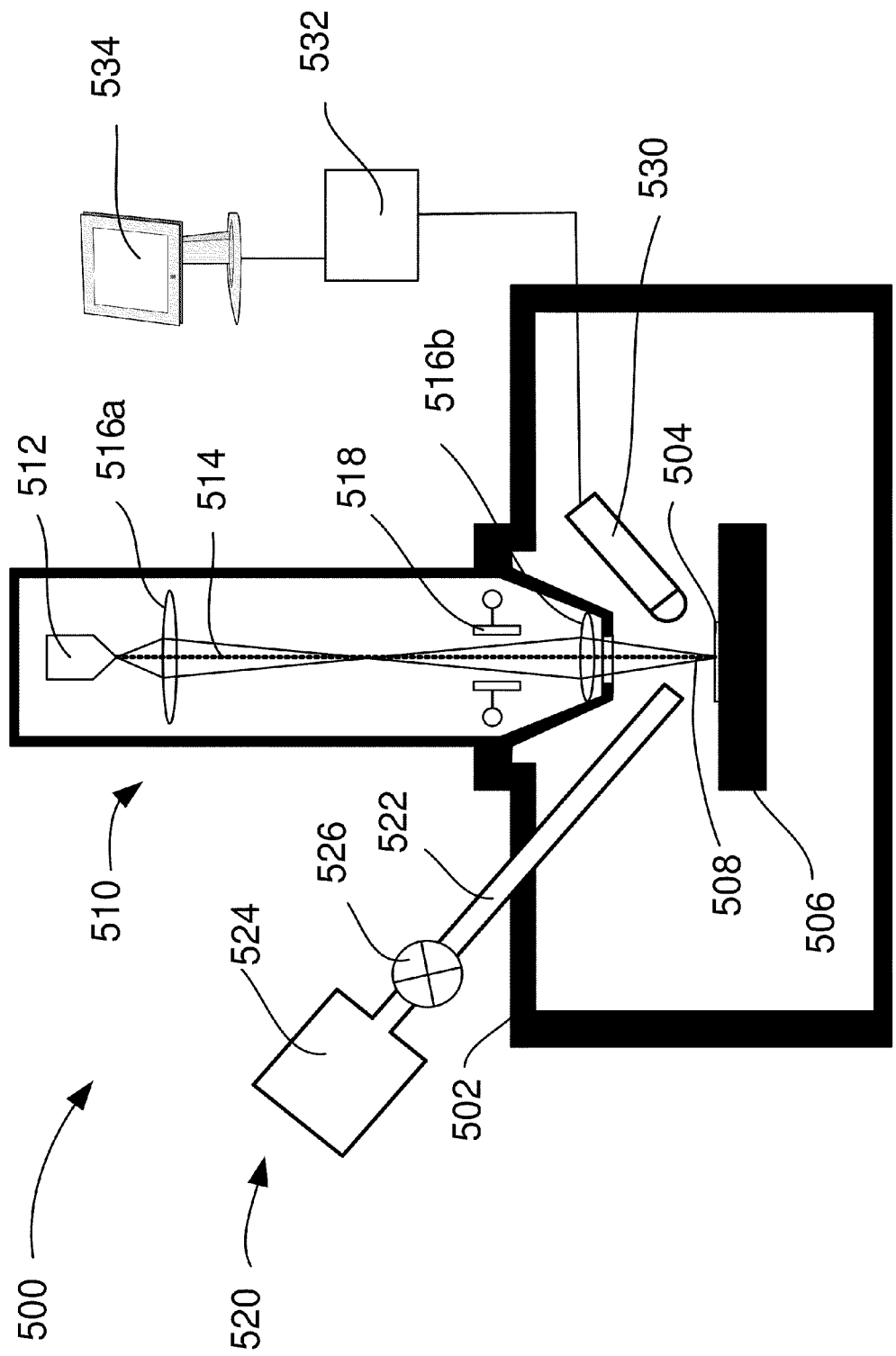

FIG. 5 schematically shows an apparatus equipped to perform the method according to the invention.

FIG. 5 shows a FIB 500 which comprise an evacuable chamber 502 upon which a FIB column 510 is mounted. The FIB column includes an ion source 512 for producing a beam of ions along an optical axis 514. The beam is focused by lenses 516a and 516b and can be deflected by a deflector 518. The FIB column thus produces a focused ion beam 508.

A work piece 504 is placed on a work piece holder 506. The work piece holder is equipped to position the work piece with respect to the focused ion beam 508 produced by the FIB column.

The FIB is further equipped with a Gas Injection System (GIS) 520. The GIS comprises a capillary 522 though which a fluid may be directed to the work piece, and a reservoir 524 containing the fluid. A valve 526 can regulate the amount of fluid directed to the work piece. Such a fluid may be used for depositing a protective layer on the work piece, or another GIS with another fluid may be used to enhance the milling.

The FIB is further equipped with a detector 530 for detecting secondary radiation. This may, for example, be an Everhart-Thornley detector for detecting secondary electrons, or a semiconductor device such as a photodiode. Also other detectors, including detectors that convert secondary ions to electrons to be detected, are known.

The signal of the detector is fed to a controller 532. This controller is equipped with a computer memory for storing the data derived from this signal. The controller also controls other parts of the FIB, such as the lenses 516, the deflector 518, the work piece holder 506, the flow of the GIS 520 and the vacuum pumps evacuating the chamber 502 (vacuum pumps not shown). Therefore the controller is equipped to position the ion beam on the work piece. The controller may form an image of the stored data on monitor 524.

It is noted that, although the invention is explained in FIG. 5 using a FIB, the invention can likewise be used with, for example, an apparatus using an electron beam, or an apparatus using both an ion and an electron beam. The invention may be used with an apparatus using other types of detectors, GIS systems, lenses, deflectors, particle sources and the like.

We claim as follows:

1. A method of milling and imaging a work piece, the work piece showing a surface, the method comprising:
    placing the work piece in an evacuated environment;
    directing a focused particle beam to the surface, such that the beam impinges on the work piece substantially parallel to the face of the work piece;
    scanning said beam over the surface in a predetermined pattern to irradiate points of the work piece, thereby milling the work piece, wherein the irradiated points form a single curve that is repeatedly scanned, and wherein during each scan material is milled from a different distance from the surface;
    acquiring a signal from a detector detecting radiation emerging from the work piece in response to the particle beam impinging on the work piece, and
    storing data derived from the signal for the multiple scans of the curve over the work piece in a computer memory, the data thus forming a representation of a face of the work piece, as a result of which the face is in one direction defined by the direction of the beam of particles and in the other direction defined along the curve.

2. The method of claim 1 in which the beam of particles impinges substantially perpendicular to the surface.

3. The method of claim 1 in which the data is used to form an image.

4. The method of claim 1 in which the curve is a line segment, as a result of which the face is a rectangular face.

5. The method of claim 1 in which the curve is a loop, as a result of which the face is a curved face.

6. The method of claim 5 in which the loop is a circle, as a result of which the face is a cylindrical face.

7. The method of claim 1 in which the detected radiation comprises charged particles emerging from the work piece.

8. The method of claim 1 in which the focused particle beam is a focused charged particle beam.

9. The method of claim 1 in which the milling comprises gas assisted milling or gas assisted etching.

10. The method of claim 1 in which the data stored in the computer memory is compared to other data to determine an endpoint action.

11. The method of claim 10 in which the other data is data generated using a CAD model.

12. The method of claim 1 in which the curve is build up of a number of dwell points, the beam of particles directed to each of the dwell points for a predetermined dwell period, after which the beam of particles is directed to the next dwell point.

13. The method of claim 12 in which for each dwell period one data-point is stored in the computer memory.

14. The method of claim 12 in which each dwell period is divided into a number of sub-dwell periods, each sub-dwell period resulting in a data-point in the computer memory, each data-point corresponding to a different distance from the surface.

15. The method of claim 1 in which, prior to directing the beam to a point on the curve, an adjacent point is milled, the adjacent point located at a position such that, when directing the beam to the point on the curve, the beam does not hit the part of the face between the surface of the work piece and the part of the work piece that is milled.

16. Software for programming a particle-optical apparatus, the particle-optical apparatus equipped to scan a finely focused particle beam over a work piece and to store data derived from a signal from a detector detecting secondary radiation emerging from the work piece in response to the impinging particle beam, the apparatus equipped with a programmable controller for controlling the apparatus, wherein the software comprises code for programming the programmable controller to perform the method defined in claim 1.

17. A method of milling and imaging a work piece having a first vertical face perpendicular to its horizontal surface, comprising:
    repeatedly scanning a focused particle beam over the surface of the work piece near the first face of the work piece in a pattern of a single line, thereby milling the line deeper into the surface with each scan and exposing a second vertical face;
    acquiring a signal from a detector detecting radiation emerging from the work piece in response to the particle beam impinging on the work piece, and
    storing data derived from the signal for the multiple scans of the line over the work piece in a computer memory, the data thus forming a representation of the second face of the work piece, as a result of which the second face is in one direction defined by the direction of the beam of particles and in the other direction defined along the milled line.

18. The method of claim 17 in which scanning a focused particle beam over the surface of the work piece includes scanning a focused particle beam over the surface of the work piece perpendicularly.

19. The method of claim 17 in which the curve is build up of a number of dwell points, the beam of particles directed to each of the dwell points for a predetermined dwell period, after which the beam of particles is directed to the next dwell point.

20. The method of claim 17 in which the signal acquired data is used to form an image.

21. The method of claim 17 in which:
repeatedly scanning a focused particle beam includes repeatedly scanning a focused ion beam; and
the signal acquired during each of the multiple scans of the line is used to form a line in an image of a vertical face of the sample, the signal being acquired while the focused ion beam in milling the sample.

22. The method of claim 17 in which repeatedly scanning a focused particle beam includes thinning a lamella using a focused ion beam.

23. The method of claim 22 further comprising using the acquired signal to form an image of a vertical face and evaluating the image to determine when to stop thinning the lamella.

* * * * *